US006727451B1

United States Patent
Fuhr et al.

(10) Patent No.: US 6,727,451 B1
(45) Date of Patent: Apr. 27, 2004

(54) METHOD AND DEVICE FOR MANIPULATING MICROPARTICLES IN FLUID FLOWS

(75) Inventors: Günter Fuhr, Berlin (DE); Rolf Hagedorn, Berlin (DE); Torsten Müller, Berlin (DE); Thomas Schnelle, Berlin (DE); Gabriele Gradl, Berlin (DE)

(73) Assignee: Evotec Technologies GmbH (DE)

( * ) Notice: Subject to any disclaimer, the term of this patent is extended or adjusted under 35 U.S.C. 154(b) by 0 days.

(21) Appl. No.: 09/673,034

(22) PCT Filed: Apr. 8, 1999

(86) PCT No.: PCT/EP99/02380

§ 371 (c)(1),
(2), (4) Date: Nov. 30, 2000

(87) PCT Pub. No.: WO99/52640

PCT Pub. Date: Oct. 21, 1999

(30) Foreign Application Priority Data

Apr. 8, 1998 (DE) .......................... 198 15 882

(51) Int. Cl.⁷ .................. B01D 57/02; G01N 27/447
(52) U.S. Cl. .................. 209/130; 204/547; 204/519; 204/555
(58) Field of Search .................. 209/130; 204/547, 204/518, 519, 560, 555

(56) References Cited

U.S. PATENT DOCUMENTS

| | | | | |
|---|---|---|---|---|
| 4,839,032 A | * | 6/1989 | Whitlock | 209/11 |
| 5,039,426 A | | 8/1991 | Giddings | 210/695 |
| 5,118,407 A | * | 6/1992 | Beck et al. | 209/127.2 |
| 5,454,472 A | | 10/1995 | Benecke et al. | 209/127.1 |
| 5,626,734 A | | 5/1997 | Docoslis et al. | 204/547 |
| 5,837,115 A | * | 11/1998 | Austin et al. | 204/450 |
| 5,909,813 A | * | 6/1999 | Stelzer | 209/128 |
| 6,054,035 A | * | 4/2000 | Kambara | 204/601 |
| 6,106,685 A | * | 8/2000 | McBride et al. | 204/600 |
| 6,261,430 B1 | * | 7/2001 | Yager et al. | 204/450 |
| 6,280,589 B1 | * | 8/2001 | Manz et al. | 204/451 |
| 6,296,020 B1 | * | 10/2001 | McNeely et al. | 137/806 |
| 6,310,309 B1 | * | 10/2001 | Ager et al. | 424/401 |
| 6,328,869 B1 | * | 12/2001 | Ogle | 204/600 |

(List continued on next page.)

FOREIGN PATENT DOCUMENTS

| | | | | |
|---|---|---|---|---|
| DE | 19605830 | | 2/1996 | |
| EP | 0230899 | | 1/1987 | |
| FR | 489249 | * | 1/1919 | 209/130 |
| WO | 9810267 | | 3/1998 | |

OTHER PUBLICATIONS

"Microfabricated Flow System for Magnetic Cell and Particle Separation" by Gert Blankenstein; Mikroelektronik Centret (MIC) Technical University of Denmark; pp. 233–245. 1997.

"Radio Frequency Microtools for Particle and Live Cell Manipulation" by Fuhr et al.; Natur WissenschaftenAufsätze 81, pp. 528–535 (1994).

"Observation of a single–beam gradient force optical trap for dielectric particles" by Ashkin et al. (Reprinted from Optics Letters, vol. 11, pp. 288–890, May 1986.

*Primary Examiner*—Donald P. Walsh
*Assistant Examiner*—Daniel K Schlak
(74) *Attorney, Agent, or Firm*—Baker Botts LLP

(57) ABSTRACT

To manipulate microparticles in a fluid that intersects a first channel or several first channels as a stream, one or more microparticles (14) are exposed to electrical field barriers that change their direction from the direction of flow toward the edge of the flow to a lateral hole (17) of the respective first channel. As a result, microparticles can be moved back and forth between streaming fluids. Preferred applications include treatment, separating, sorting or confinement procedures.

16 Claims, 7 Drawing Sheets

U.S. PATENT DOCUMENTS 6,368,871 B1 * 4/2002 Christel et al. ............. 436/180
6,413,782 B1 * 7/2002 Parce et al. ................. 204/451
6,444,106 B1 * 9/2002 Mcbride et al. ............ 204/450
6,447,727 B1 * 9/2002 Parce et al. ................. 204/600
6,451,264 B1 * 9/2002 Bhullar et al. .............. 204/451
2002/0023841 A1 * 2/2002 Ahn et al. .................. 204/547
2002/0108889 A1 * 8/2002 Fujii et al. .................. 209/130
2003/0178310 A1 * 9/2003 Gawad et al. ............. 204/547

* cited by examiner

METHOD AND DEVICE FOR MANIPULATING MICROPARTICLES IN FLUID FLOWS

BACKGROUND OF THE INVENTION

The invention relates to a system for manipulating microparticles in streaming fluids, in particular a procedure for moving microparticles, e.g., biological cells, between various fluids, e.g., for sorting, treatment or confinement purposes, and a microsystem device for implementing the procedure.

Many biological, medical, pharmacological, and even non-biological applications place importance on precise loading with substances and non-contact confinement of microscopic particles, such as biological cells or cell clusters, latex particles or other microbeads in a free liquid. The most frequent method is to grow cells on a solid substrate, which is then rinsed with the required precision using a solution, or to have confinement take place on a sieve or capillary openings. The disadvantage to this procedure is the mechanical surface contact and the difficulty involved in sequentially processing numerous objects in identical fashion. Particular difficulties are encountered in exposing microscopic objects to another solution without surface contact for very short and adjustable times, and then returning them to the original medium. This has previously been achieved at the expense of complicated washing and centrifugation stages.

Use is also made of so-called "laser tweezers", with which particles can be held in position in a free solution with micrometer precision, or shifted to a defined extent (see A. Ashkin et al. in "Optics Lett.", Vol. 11, p. 288 (1986)). The disadvantage is that this principle requires a considerable outlay of external equipment, which runs counter to the advantages of system miniaturization and is cost-intensive. In addition, the object is strained in the focal area.

One alternative involves electrical microfield cages, in which microparticles and cells can be held in place similarly to "laser tweezers" via polarization forces (G. Fuhr et al. "Naturwiss.", Vol. 81, p. 528 (1994)). However, only one solution is situated in such systems, so that the microparticles can only be transferred to another medium via liquid exchange, which requires longer times until the next use and possibly separate cleaning stages. A particle can be held in a confined or parked position by means of a laser tweeter, but it makes no sense from a technical standpoint for several particles. In addition, the object is exposed to a permanent beam load for the time parked.

Magnetically charged particles are transferred from one solution into another in micro systems via magnetic fields or ultrasound sources acting at a right angle to the channels (see G. Blankenstein in "Scientific and Clinical Applications of Magnetic Carriers", published by Hafeli et al., Plenum Press New York 1997 (Ch. 16, pp. 233). Both techniques are only suitable for miniaturization under very limited conditions, do not permit focusing the forces acting on the particles, and are difficult to convert in an integrated form using techniques in semiconductor structuring procedures. In addition, this technique is associated with a load with magnetic particles that might be physiologically disruptive for biological objects.

DE-OS 41 43 573 discloses a device for separating mixtures of microscopic particles in a liquid, in which the particles are exposed to electrical fields of traveling waves, during which influence the particles are tapped from a stream of liquid. This device has the following disadvantages. Numerous microelectrodes are required to generate the traveling waves, thus resulting in a complex structure with the respective separate drive circuits. The microelectrodes are situated in an area substantially larger than the particles to be tapped. The traveling waves trigger temperature gradients in the liquid that give rise to disruptive transverse flows. These transverse flows and any other existing flow inhomogeneities prevent the particles from moving along defined paths. To compensate for this locally undefined tapping, it must extend over a relatively wide area in the direction of flow. This in turn results in entire particle groups getting tapped, or the particles must move through the micro system with great distances, thus delaying the processing of large number of particles.

Therefore, the known techniques could previously only be used on a restricted basis, if at all, to transfer microparticles from one liquid to one or more others and back, or to effect a non-contact intermediate storage in a micro system.

SUMMARY OF THE INVENTION

Accordingly, the object of the invention is to provide an improved procedure for manipulating microparticles in fluid streams that has an expanded range of application, and in particular can be used serially and parallel at a high velocity, and also enables electrically controllable procedures for the non-contact confinement and transfer of microparticles in various media. The object of the invention is also to provide a device for executing the procedure, which has a simplified design along with a simplified and reliable drive circuit, and is set up to form defined paths of movement for the microparticles to be manipulated.

This object is achieved by a procedure with the features set forth in claim 1 and a device with the features set forth in claim 9. Advantageous embodiments of the invention are described in the dependent claims.

The invention is based on the idea of subjecting microparticles to electromagnetic forces in a streaming fluid. The electromagnetic forces are exerted by at least one electrical field barrier, against which the microparticles are moved with the streaming fluid, and which causes the microparticles to move in a direction deviating from direction of flow. The electrical field barrier is generated, for example, with at least one pair of strip-shaped microelectrodes, which is situated at opposing boundaries of the streaming fluid and exposed to a high-frequency alternating voltage. The selected amplitude for the alternating voltage of field barrier is high enough to prevent the microparticles to be deflected from getting between the electrodes. The fluid with the microparticles suspended therein flows through a channel with at least one lateral hole, to which at least one microparticle is moved along the electric field barrier. The hole is bordered by another channel with a streaming fluid or looped branch (so-called parking loop) of the first channel. The streaming fluids of the respective channels come into contact at the hole. However, the fluids do not become mixed together if the streaming fluid system is implemented with laminar flows. The laminar flows are advantageously implemented in micro systems or with capillary channels. One particular advantage to the invention is that the streaming fluids at the openings between the channels form boundary surfaces that the microparticles to be manipulated can pass through.

The electromagetic field forces are generally exerted via 3-dimensionally distributed electrode arrays through or at the holes between the channels for transferring the objects into one or several adjacent channels or parking loops by applying high-frequency voltages given a permanent hydrodynamic flow through the system. The electrode arrays acting as deflecting systems can be actuated from a computer, permitting minimal manipulation times in the ms range. The movement can take place in a free solution without any mechanical contact or guidance of the object. The procedure involves no interference and uses the conventional optical measuring methods, thereby avoiding damage to living biological objects, e.g., cells. The time for which the particles reside in the compartments or channel sections can be externally set. Typical path diameters or deflections lie within a range of 50 nm and several 100 µm or more. No feedback check or observation of the objects is required (but can be additionally performed).

Special advantages to the invention are that a highly precise, reliable and rapid particle manipulation is achieved with a relatively simple electrode configuration (in the simplest case: with one pair of electrode strips). Disruptive transverse flows are avoided. The electrodes can be exposed to a sufficiently high alternating voltage, so that the particles reliably stay on the side of the field barrier located upstream, and are routed to the lateral hole. The electrodes have characteristic dimensions smaller than or equal to the dimensions of the particles to be manipulated. Manipulating the particles according to the invention makes it possible to move the particles in and out of the flow, i.e., to also return particles from an adjacent flow.

BRIEF DESCRIPTION OF THE DRAWINGS

Additional advantages and details of the invention are described below with reference to the attached drawings. Shown on.

The examples shown always involve three-dimensional configurations of microelectrodes, with which barrier-type electric high-frequency fields are generated in channels. The perspective view shows an example of such a system in FIG. 1. The examples show only 1, 2 or 3 channel systems. However, the invention can be expanded by any other kinds of combinations desired. The invention will be explained based on streaming liquids, but can also be implemented with other fluids given sufficiently strong field forces. The invention is not limited to the depicted flat channel walls, but can also be implemented using channels with other, e.g., round, cross sections.

DETAILED DESCRIPTION OF THE INVENTION

Figure 1:
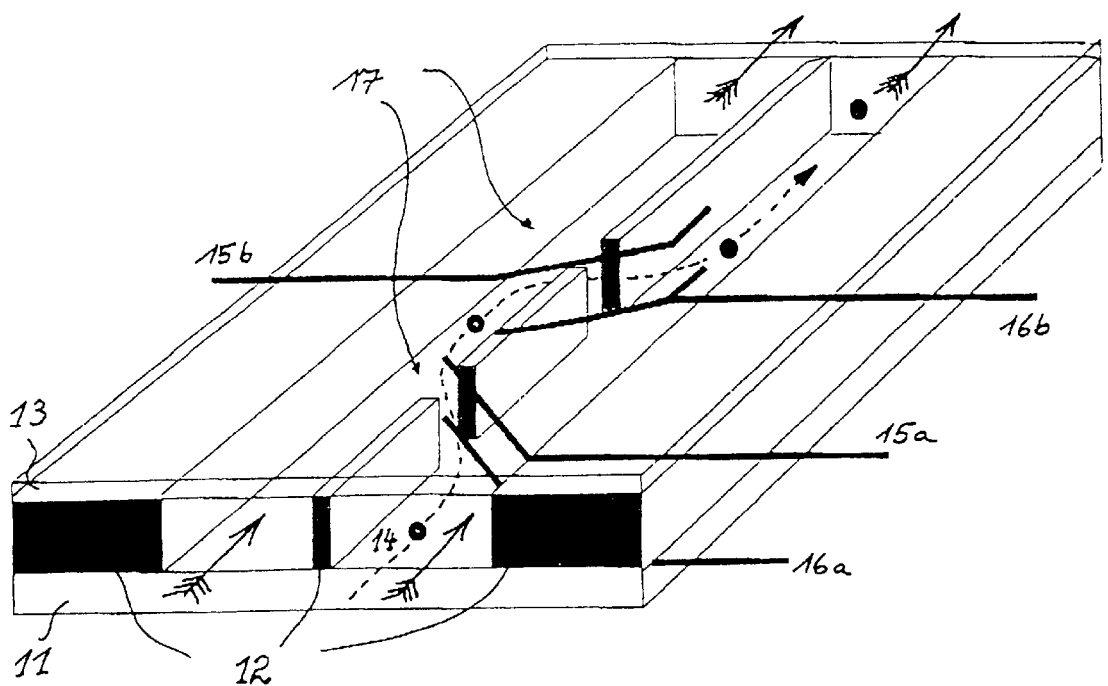
FIG. 1 is a perspective view of a first embodiment of a streaming fluid system according to the invention.

FIG. 1 shows a perspective view (cutout) of a 2 channel system comprised of a bottom substrate 11, on which the microelectrodes or electrode sections 16a, 16b (denoted with straight leads) are arranged in a planar fashion, the spacer 12 forming the channel walls, and a cover substrate 13 (shown as transparent, can be transparent or non-transparent in execution), on whose side facing the channel planar microelectrodes or electrode sections 15a, 15b (denoted by straight leads) are also situated.

The spacer 12 forms a right (first) and left (second) channel. The central separating wall has holes 17. An electrode configuration comprised of the respective electrode sections 15a, 16a or 15b, 16b is allocated to each hole 17. The electrode sections each extend upstream in a channel section, from the respective hole from a wall lying opposite the hole up to the hole, or preferably through the latter and into the adjacent channel. As a result, the electrode sections define a reference plane that lies perpendicularly on the surface of the bottom substrate 11 and at an angle to the longitudinal direction of the channel.

An alternating voltage (frequency: kHz to MHz, amplitude: 0.1 to 5.0 V) is applied between the electrode sections 15a, 16a and 15b, 16b. The frequency is selected as a function of the dielectric properties of the microparticles or particles in such a way that the latter exhibit a negative polarization, i.e., negative dielectrophoresis, and are repelled by the high-frequency field. As an alternative, the frequency can be selected in such a way that positive dielectrophoresis (attraction) takes place, wherein the electrode sections belonging to a hole would than have to be arranged upstream in the respective other channel. However, negative dielectrophoresis offers major advantages for the non-contact manipulation of the microparticles.

Therefore, a repelling field is formed as a barrier in the area of the mentioned reference plane, which exerts a force on the particles toward hole 17 due to the bias relative to the longitudinal direction of the channel in conjunction with the flow.

In the present example, various liquids flow through the channels in the same direction (arrows). Suspended particles (e.g., living cells) are washed in with a carrier liquid via the first channel. A treatment liquid (e.g., a charging medium with a dissolved substance with which the particles are to be charged) flows through the second channel.

A particle 14 moves along the path shown with the dashed line. For purposes of defined treatment, the microparticles are moved through the first hole 17 into the second channel. The particles can be conveyed into the charging medium for a defined period of time as the result of the flow rate and the arrangement of deflecting electrode sections 15a, 16a and 15b, 16b. As a rule, this process takes place at flow rates of several to several hundred µm/s. Therefore, the retention time in the charging medium lies in the ms to s range, depending on the distance of the deflecting electrodes.

Return from the second channel to the first channel takes place in a similar fashion at the second hole 17.

Figure 2:
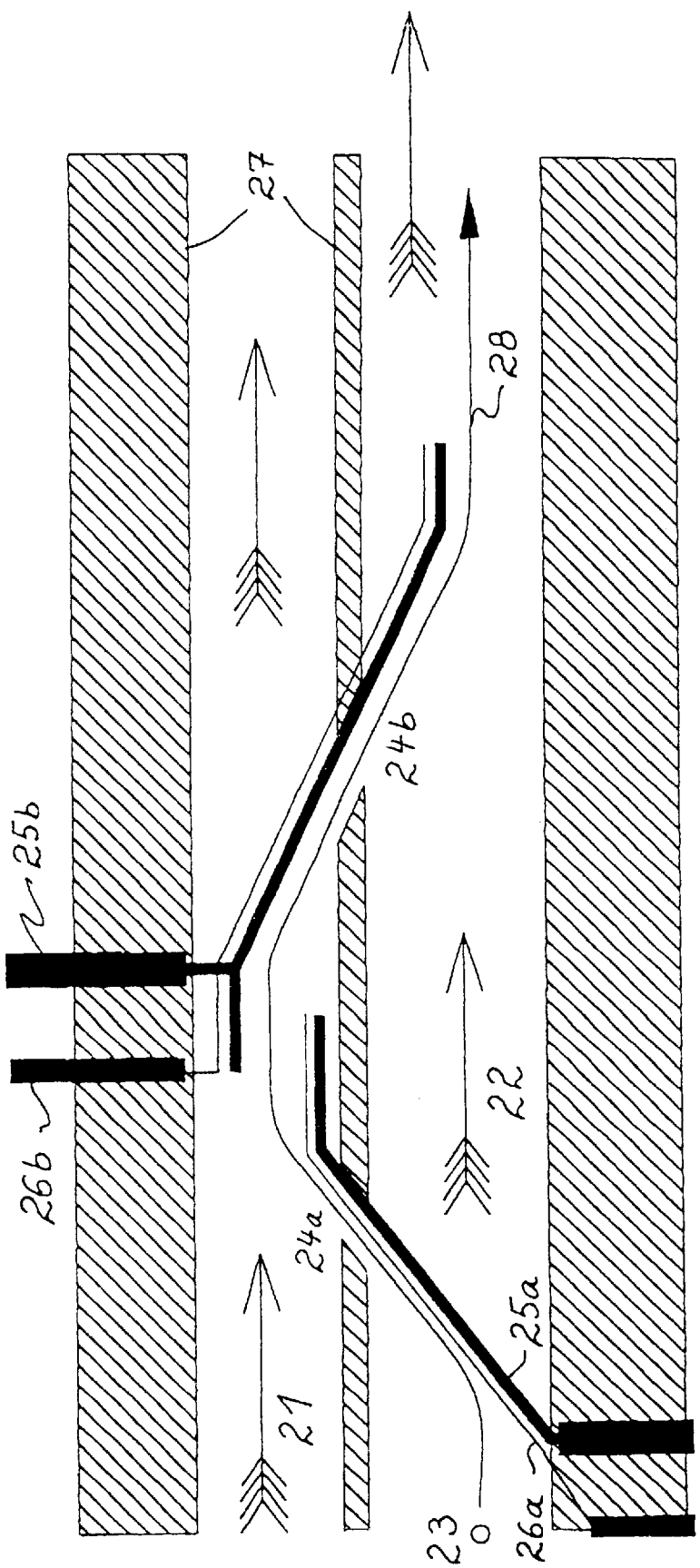
FIG. 2 is a top view of a streaming fluid system according to FIG. 1.

FIG. 2 shows a top view of the system described in FIG. 1. The two channels 21, 22 are traversed from left to right. The channel walls are formed by a spacer 27. The particles 23 will follow path 28 with the field activated. Otherwise, they will not switch over to the adjacent channel. Electrode sections 25a, 26a and 25b, 26b (also called deflecting electrode pairs) are here shown diagrammatically, i.e., the thin line denotes the lower electrode plane 26a, 26b, and the thicker line denotes the upper electrode plane 25a, 25b. The width of the electrodes can range from several 100 nm to about 100 µm (typically 10 to 20 µm). The size of the particles 23 (nm to mm) determines the height of the channels. Favorable values are roughly 2 to 20 times the particle diameter. To minimize electrical losses, the leads to the deflecting electrodes must not be arranged together, but rather offset to the side as much as possible. If the deflecting unit 25b, 26b is deactivated, the particles remain in the solution of channel 21. The retention time in channel 21 can be determined via the distance of holes 24a, 24b or the flow rate.

The channels have dimensions that can be selected as a function of the fluid viscosity (provision of laminar flows). Preferred characteristic dimensions lie within the sub-$\mu$m to mm range, preferably several $\mu$m to 0.5 mm, e.g., 200 $\mu$m.

The electrode sections are shown as strips, but can exhibit any other shape that ensures that the force will reach the holes in the channel wall.

Figure 3:
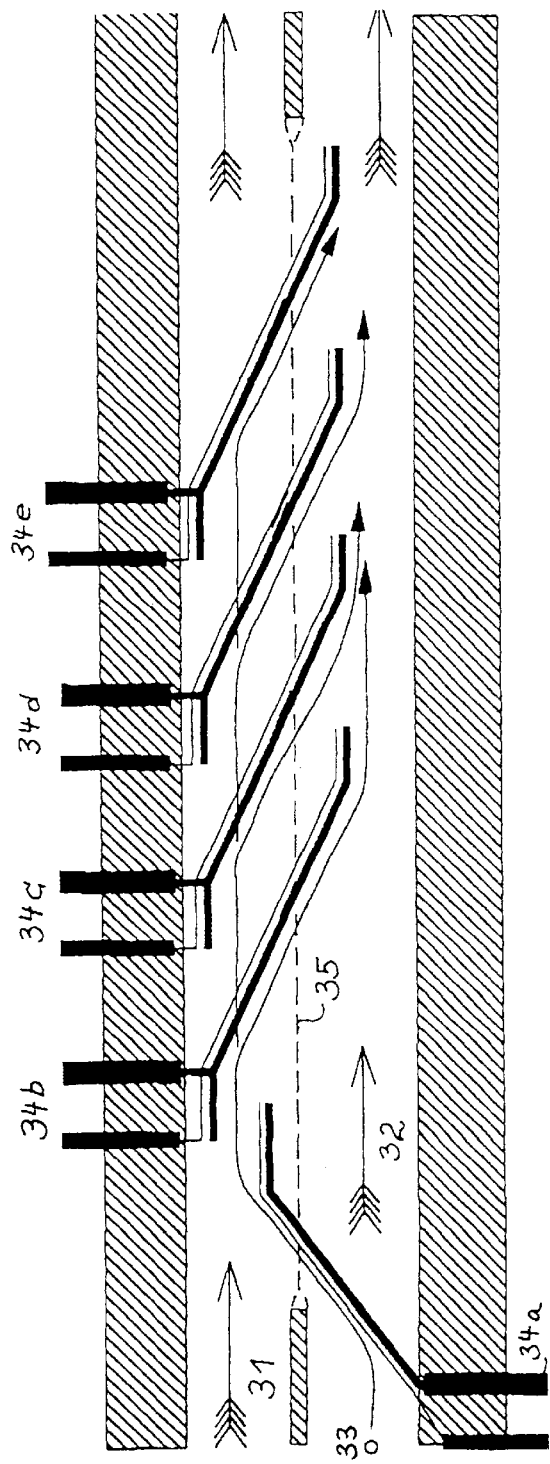
FIGS. 3 to 5 are top views of streaming fluid systems according to a second, third and fourth embodiment of the invention.

FIG. 3 shows a special advantage of the invention. Specifically, no mutual disruption of streaming liquids (no mixing together) takes place in microchannels with a diameter of <½ mm. Flows remain laminar over large distances. In the example shown, this effect is utilized to temporarily transfer the particles from FIGS. 1 and 2 to another solution. The separating wall between the channels 31 and 32 here forms a hole 35 several $\mu$m or several hundred $\mu$m in length. When the flow passes through the channel in the same direction, no mixing together takes place at this contact surface for the reasons cited above. A particle 33 can be transferred from channel 32 to channel 31 via the deflecting unit 34a. The retention time in the medium of channel 31 can be determined via the deflecting units 34b–e. The particles move at the trajectories indicated with the arrows.

Figure 4:
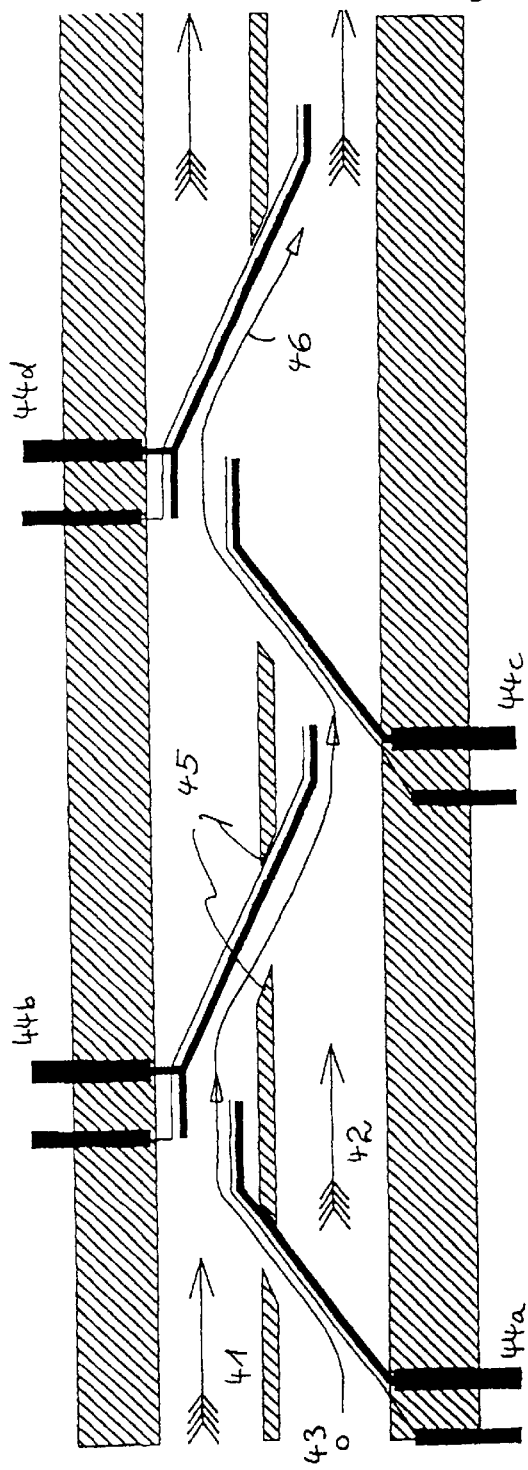

FIG. 4 shows a device in which a particle 43 can be transferred from channel 42 to channel 41 and back repeatedly. The system can also have a more forward design, however. The particles travel along path 46. The first element 44a, 44b has a separating wall 45. The second deflecting device 44c, 44c can work without this element. Depending on the distance of the deflecting system, the separating wall element need also not be used in the first transitional area.

Figure 5:
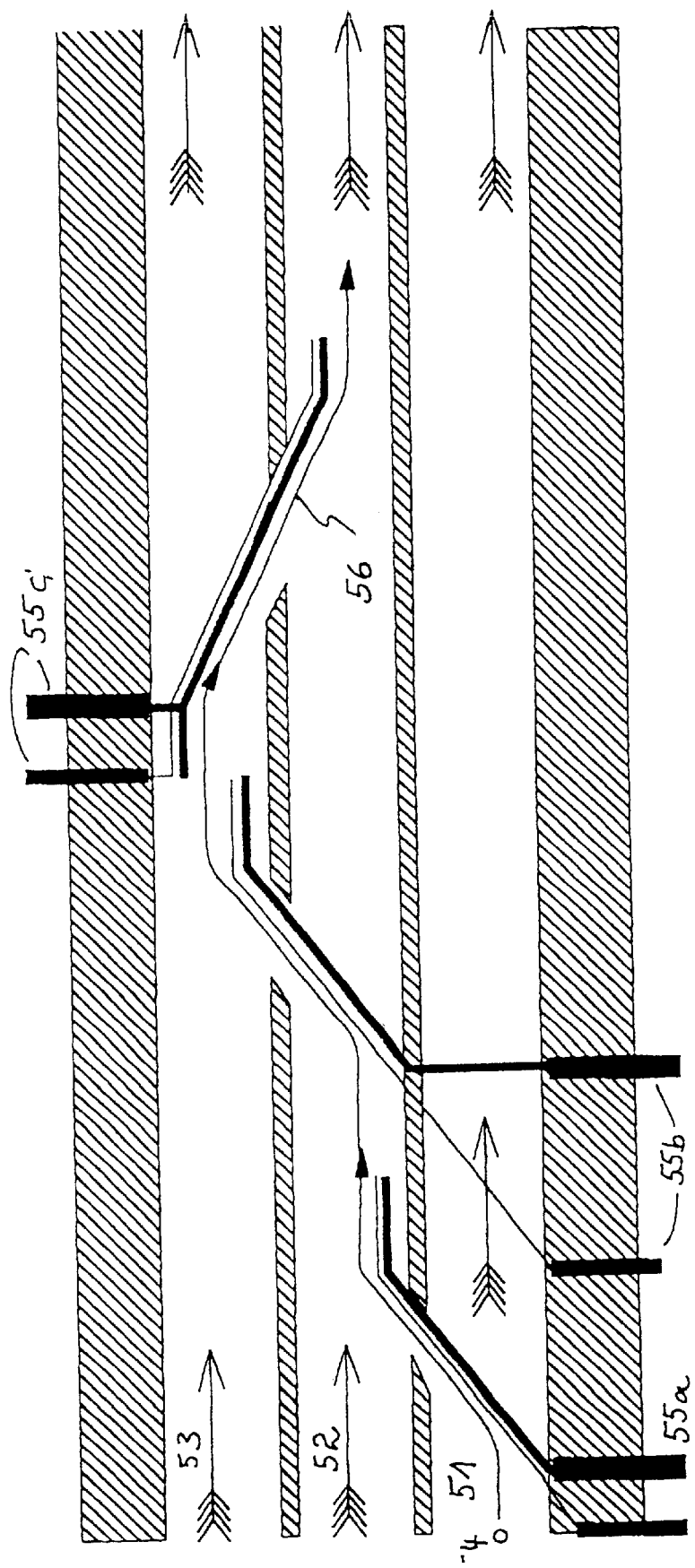

For biochemical and cellular biological/medical tasks, it is frequently important to transfer objects into several liquids for a short time in a defined and controllable manner. FIG. 5 shows a 3-channel system as an example. All channels 51, 52 and 53 are traversed from left to right. The particles 54 can be transferred into the channel 52 via the deflecting system 54a, and into the channel 53 via 55b. The particle can again be returned to the channel 52 via the deflecting unit 55c. This is followed by path 56. An additional deflecting unit and hole can be arranged between the channels 51 and 52 to again return the particle to the channel 51. According to the pattern shown, a much higher number of channels and transfer elements can be implemented.

Figure 6:
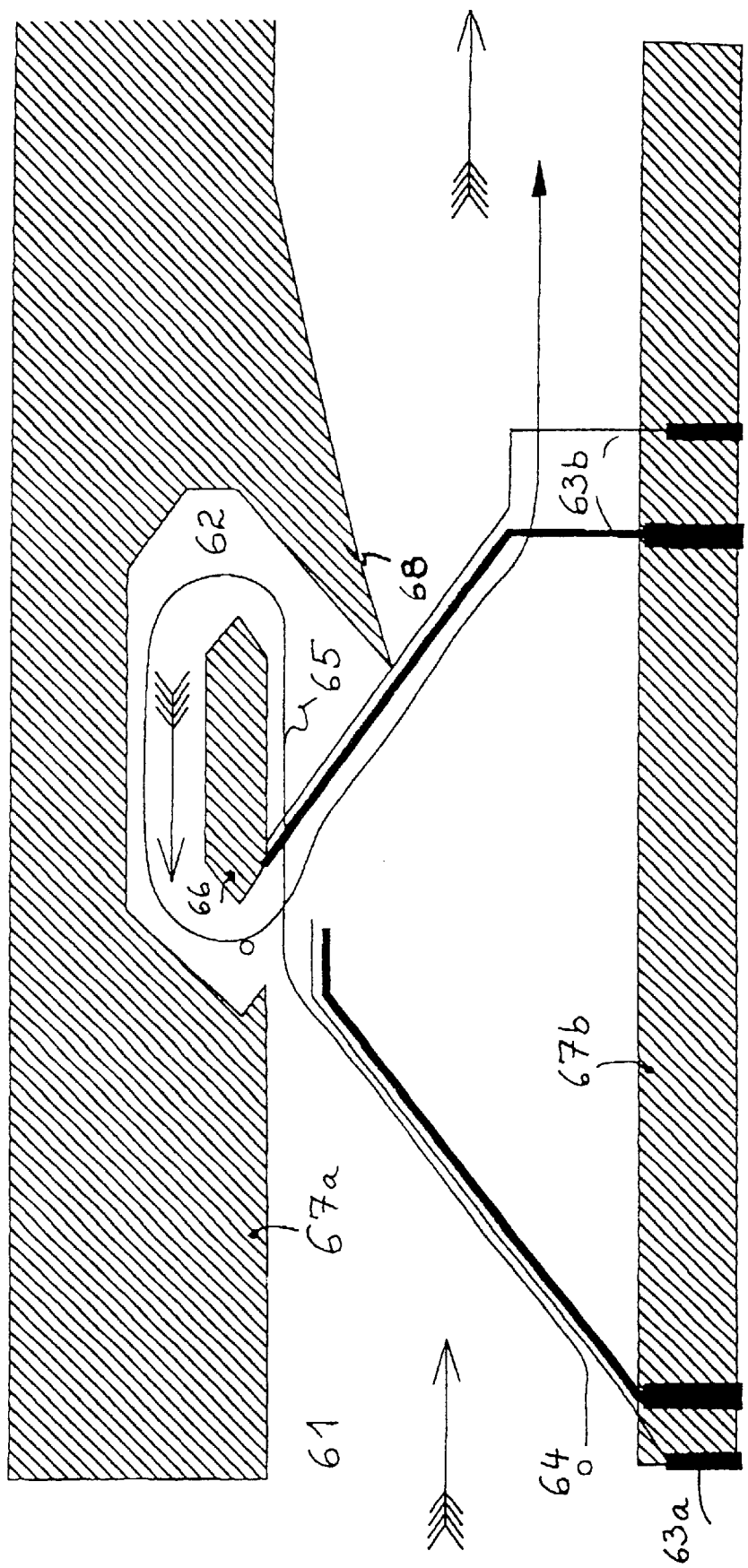
FIG. 6 is a top view of a streaming fluid system according to an embodiment with a looped branch.
Figure 7:
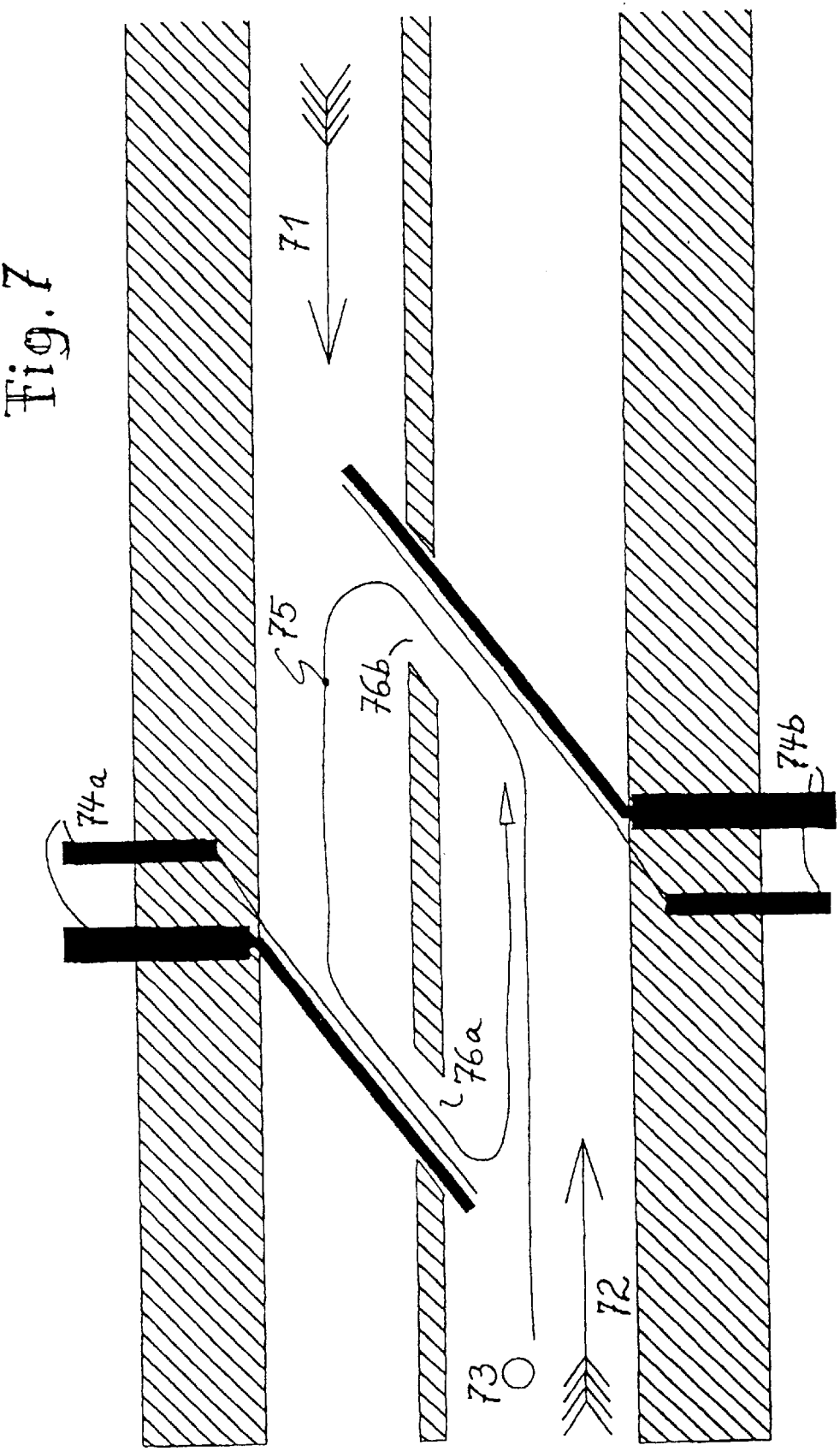
FIGS. 7 and 8 are top views of streaming fluid systems according to an embodiment of the invention with looped flows between two channels.
Figure 8:
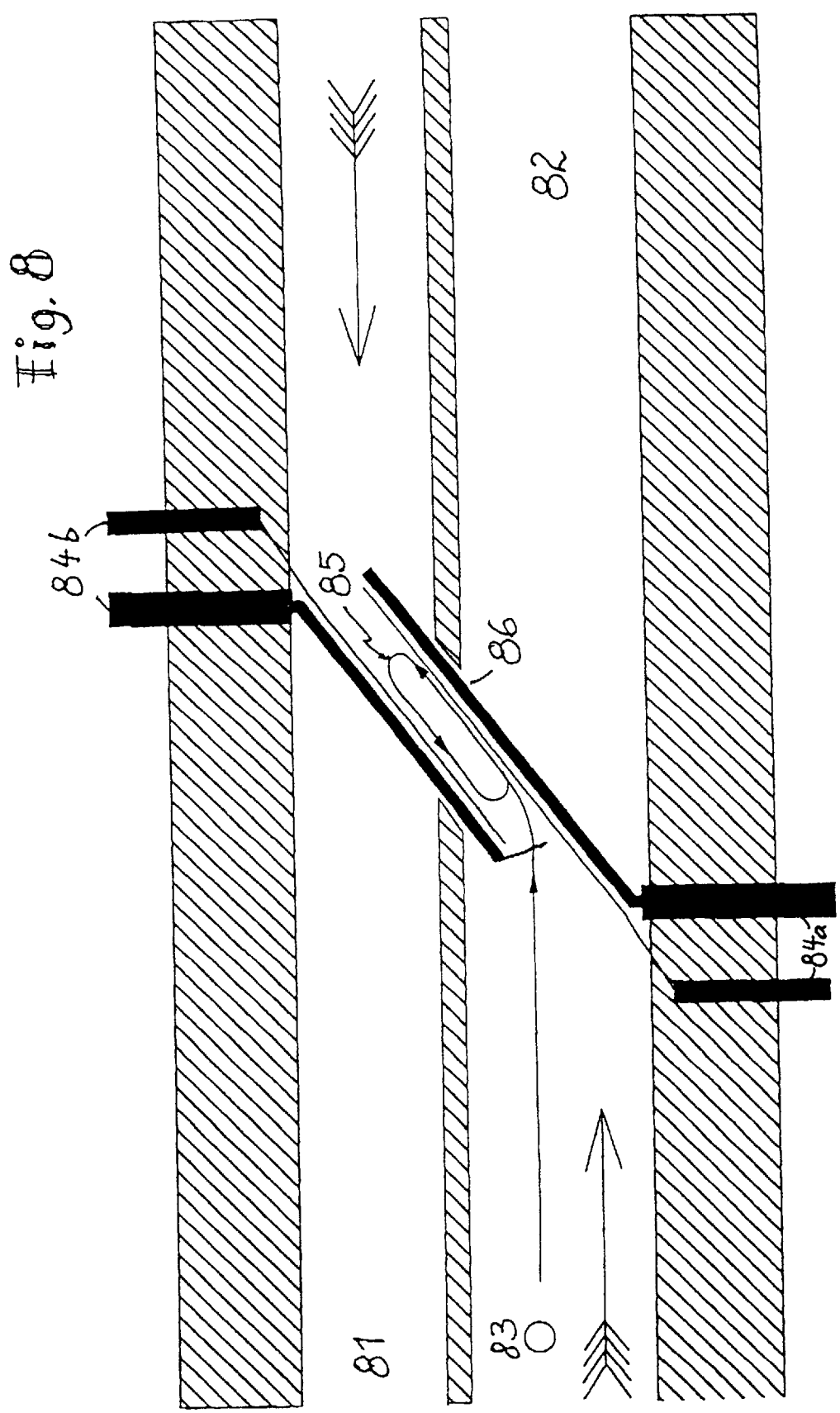

The short flow times pose a thus far unresolved problem in microfluidic systems linked with cellular biology. For example, when measuring a particle, either the flow had to be stopped, or additional particles located in the channel system would be irretrievably rinsed out. Stopping the flow gives rise to the danger of surface contact and subsequent adhesion. For this reason, it is best that parking loops be implemented for particles given a permanent flow. FIG. 6 shows such a basic element. The channel 61 is traversed from left to right. Accommodated inside one of the walls (67a) is an annular channel 62, which is formed by a spacer section 66. The spacer projects into the channel 68 a bit on the back, so that a portion of the liquid starts to circulate in the channel 62. A particle 64 can be introduced into this flow via the deflecting electrode 63a. If the deflecting electrode 63b is not actuated, it remains in the annular flow, and moves on a looped parking orbit 65. If the particle is to be removed, the deflecting system 63 is turned off, and the particle leaves the parking loop.

The particle parking loop and defined transfer to another solution are combined by having two deflecting systems 74a, 74b projecting through holes in the shared channel wall into the respectively adjacent channel 71, 72. Given an opposed flow through the channels 71, 72, a particle 73 would move to a circular orbit 75, in which several particles are accommodated at the same time. Turning off the HF voltage on one or both deflecting systems allows the particles to exit into one or the other streaming solution. At the same time, this device offers the advantage of being able to use liquids of differing composition in both channels. The number of particles orbits makes is possible to set and measurably reproduce the time for which it is to be exposed to the respective substance. Additional detection means can be used at one or several locations to determine the orbiting time and number of trapped particles. This can take place optically, or by means of a "Coulter Counter" at the holes 76a, 76b. One can also conceive the system as expanded, comprised of numerous such elements in series and parallel. Therefore, it is suitable for confining numerous particles, acquiring their location and treating them in a comparable manner.

Of particular interest are very short retention times or parking loops, which could only be occupied in large numbers and each by only one or a few particles at a time. To this end, the deflecting systems 84a, 84b are to be placed as close together and in a hole 86 between the channels 81, 82. If both channels are now traversed in an opposite direction, the particle 83 will follow the trajectory 85. The minimal diameter of the orbit equals roughly twice the particle diameter. Assuming that submicrometer particles, such as viruses, can be trapped and periodically transferred from one solution to another in this way, the shortest periods per orbit measure several ms.

What is claimed is:

1. A procedure for manipulating microparticles in a fluid, which fluid runs as a directional stream through at least a first channel with at least one lateral hole, and at least one electrode configuration, which is set up to generate at least one electrical field barrier, wherein the electrode configuration is capable of being actuated by exposure to an electrical high-frequency voltage in such a way as to form that at least one electrical field barrier that intersects the stream, wherein during exposure to the at least one electrical field barrier one or several microparticles are prevented from passing the electrode configuration, and wherein the microparticles on an upstream side of the electrode configuration are subjected to a change of movement in a direction different from that of a direction in which the stream flows, and directed toward the at least one lateral hole at an edge of the stream, wherein the at least one lateral hole forms a transitional area in which the microparticles are moved in streaming fashion between the first channel and at least one adjacent second fluid-containing channel or branch, in which each microparticle is moved under influence of (a) exposure to the electrical high-frequency voltage between at least two electrodes of the electrode configuration, and (b) exposure to the streaming forces in the fluid into the transitional area, and further (c) exposure to the streaming forces of the fluid flowing in the respective adjacent second channel or branch.

2. The procedure according to claim 1, in which a plurality of locally-bounded high-frequency electrical fields are generated in channel sections, and wherein each of the channel sections borders a transitional area.

3. The procedure according to claim 1, in which the fluid streaming in the channels and branches forms a laminar streaming flow.

4. The procedure according to claim 1, in which microparticles from the first channel are sorted into a plurality of second channels in a particle-specific manner by forming electrical field barriers locally for each microparticle based on a preset time pattern in such a way that a specific microparticle may be directed to flow into a predetermined one of the plurality of second channels.

5. The procedure according to claim 1, in which the fluid in the first channel comprises an inert carrier liquid, and the fluid in the second channel comprises a treatment liquid, and the at least one electrical field barrier is formed such that the microparticles are (a) moved by the inert carrier liquid into the treatment liquid based on a preset time pattern, (b) treated in the treatment liquid, and then (c) moved back into the carrier liquid.

6. The procedure according to claim 1, in which the microparticles are moved from the first channel into a looped flow area based on a preset time pattern, retained in the looped flow area for a preset time, and moved back into the first channel again.

7. A streaming fluid system for manipulating microparticles in a directionally-streaming fluid, said system comprising (a) at least one first channel for receiving a first streaming fluid, said channel having at least one lateral hole and at least one electrode configuration, said electrode configuration being configured to generate at least one electrical field barrier that intersects a streaming direction of the first streaming fluid, characterized by the fact that the electrode configuration is actuable by an electrical high-frequency voltage such that the at least one electrical field barrier acts from an upstream side of the electrode configuration to guide at least one microparticle in targeted fashion toward the lateral hole; and (b) at least one second channel for receiving a second streaming fluid, said second channel having at least one lateral hole forming a transitional area with the lateral hole of the first channel.

8. The streaming fluid system according to claim 7, in which said second channel has at least one additional electrode configuration set up to form at least one electrical field barrier transverse to the streaming direction in the first channel and wherein the transverse electrical field barrier acts to move at least one microparticle toward a second lateral hole.

9. The streaming fluid system according to claim 7, wherein said first and second channels comprise substantially-straight capillary channels separated by a separating wall, and wherein the at least one lateral hole is formed in said separating wall.

10. The streaming fluid system according to claim 9, in which for each lateral hole there is formed at least two transitional areas, and wherein each hole forms at least two transitional areas each with an electrode configuration.

11. The streaming fluid system according to claim 7, in which said at least one electrode configuration comprises a plurality of electrode sections that are attached to a wall of said first channel, and wherein said electrode sections extend from a side of said first channel opposite of the at least one lateral hole, and wherein said extension is in a direction upstream toward the at least one lateral hole.

12. The streaming fluid system according to claim 11, in which said plurality of electrode sections are band-shaped, and extend into the at least one second channel.

13. The streaming fluid system according to claim 11, in which at least two parallel ones of said plurality of electrode sections correspond to a transitional area at opposing areas of a channel wall.

14. The streaming fluid system according to claim 7, in which said second channel comprises a looped branch from said first channel.

15. The streaming fluid system according to claim 7, in which a plurality of sets of first channels and second channels are provided, said channels being connected via transitional areas, and wherein each of said transitional areas comprise an electrode configuration.

16. A method of using a streaming fluid system as a device selected from the group consisting of: a sorting or separating device, a treatment device, and a confinement device, wherein the streaming fluid system comprises (a) at least one first channel for receiving a first streaming fluid, said channel having at least one lateral hole and at least one electrode configuration, said electrode configuration being configured to generate at least one electrical field barrier that intersects a streaming direction of the first streaming fluid, characterized by the fact that the electrode configuration is actuable by an electrical high-frequency voltage such that the at least one electrical field barrier acts from an upstream side of the electrode configuration to guide at least one microparticle in targeted fashion toward the lateral hole; and (b) at least one second channel for receiving a second streaming fluid, said second channel having at least one lateral hole forming a transitional area with the lateral hole of the first channel, said method comprising the step of operating said streaming fluid system to achieve desired handling of at least one predetermined variety of microparticles within at least one streaming fluid.

\* \* \* \* \*